United States Patent
Komatsu et al.

(10) Patent No.: US 7,204,984 B2
(45) Date of Patent: Apr. 17, 2007

(54) ACETYLLYSINE-RECOGNIZING MONOCLONAL ANTIBODY AND PROCESS FOR PRODUCING THE SAME

(75) Inventors: Yasuhiko Komatsu, Ageo (JP); Minoru Yoshida, Kawaguchi (JP)

(73) Assignee: Japan Science and Technology Corporation, Saitama (JP)

( * ) Notice: Subject to any disclaimer, the term of this patent is extended or adjusted under 35 U.S.C. 154(b) by 327 days.

(21) Appl. No.: 10/471,475

(22) PCT Filed: Mar. 13, 2002

(86) PCT No.: PCT/JP02/02330

§ 371 (c)(1),
(2), (4) Date: Sep. 12, 2003

(87) PCT Pub. No.: WO02/074962

PCT Pub. Date: Sep. 26, 2002

(65) Prior Publication Data

US 2004/0198959 A1    Oct. 7, 2004

(30) Foreign Application Priority Data

Mar. 15, 2001    (JP) .............................. 2001-074263

(51) Int. Cl.
*C12N 15/13*    (2006.01)
*A61K 39/395*    (2006.01)
(52) U.S. Cl. ................. 424/133.1; 424/141; 530/388.1
(58) Field of Classification Search .............. 424/133.1
See application file for complete search history.

(56) References Cited

U.S. PATENT DOCUMENTS 5,849,499 A * 12/1998 Hamlin et al. ................ 435/7.1
6,118,044 A *  9/2000 Karasuyama et al. .......... 800/3

FOREIGN PATENT DOCUMENTS

WO    WO-91/02080    2/1991

OTHER PUBLICATIONS

Rudikoff et al. Proc Natl Acad Sci USA 1982 vol. 79, p. 1979.*
White, et al. Preparation of Site-Specific Antibodies to Acetylated Histones. *Methods,* vol. 19, No. 3, pp. 417-424 (1999).
Hebbes, et al. A direct link between core histone acetylation and transcriptionally active chromatin. *EMBO J.,* vol. 7, No. 5, pp. 1395-1402 (1988).
T. R. Hebbes et al., "Molecular Immunology", vol. 26, No. 9, pp. 865-873 (1989).
Y. Komatsu et al., "Journal of Immunological Methods", vol. 272, No. 1-2, pp. 161-175 (2003).

* cited by examiner

*Primary Examiner*—Christina Chan
*Assistant Examiner*—Yunsoo Kim
(74) *Attorney, Agent, or Firm*—Peter F. Corless; Christine C. O'Day; Edwards Angell Palmer & Dodge LLP

(57) ABSTRACT

Anti-acetyllysine monoclonal antibody capable of recognizing $N^\epsilon$-acetyllysine regardless of the types of the adjacent amino acids. Namely, a monoclonal antibody having a light chain comprising a constant region having the amino acid sequence represented by SEQ ID NO:1 and a variable region having the amino acid sequence represented by SEQ ID NO:2 or an amino acid sequence derived from this amino acid sequence by deletion, substitution or addition of one to several amino acids, and a heavy chain comprising a constant region having the amino acid sequence represented by SEQ ID NO:3 and a variable region having the amino acid sequence represented by SEQ ID NO:4 or an amino acid sequence derived from this amino acid sequence by deletion, substitution or addition of one to several amino acids, and being capable of recognizing $N^\epsilon$-acetyllysine in a protein regardless of the types of the adjacent amino acids, i.e., being capable of accepting adjacent amino acids over a broad range; and a process for producing this monoclonal antibody characterized by using a chemically acetylated protein as an antigen.

3 Claims, 7 Drawing Sheets

FIG. 4

SEQUENCE LISTING

<160> NUMBER OF SEQ ID NOS: 42

<210> SEQ ID NO 1
<211> LENGTH: 57
<212> TYPE: PRT
<213> ORGANISM: Mus musculus

<400> SEQUENCE: 1

Ile Lys Arg Ala Asp Ala Ala Pro Thr Val Ser Ile Phe Pro Pro Ser
1               5                   10                  15

Ser Glu Gln Leu Thr Ser Gly Gly Ala Ser Val Val Cys Phe Leu Asn
            20                  25                  30

Asn Phe Tyr Pro Lys Asp Ile Asn Val Lys Trp Lys Ile Asp Gly Ser
        35                  40                  45

Glu Arg Gln Asn Gly Val Leu Asn Ser
    50                  55

<210> SEQ ID NO 2
<211> LENGTH: 110
<212> TYPE: PRT
<213> ORGANISM: Mus musculus

<400> SEQUENCE: 2

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Asp Leu Asn Trp Tyr Leu Gln Lys Pro Gly Gln Ser
        35                  40                  45

```
Pro Gln Leu Leu Ile Tyr Arg Val Ser Asn Arg Phe Ser Gly Val Leu
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Trp Thr Phe Gly Gly Gly Thr Lys Leu Asp
            100                 105                 110

<210> SEQ ID NO 3
<211> LENGTH: 54
<212> TYPE: PRT
<213> ORGANISM: Mus musculus

<400> SEQUENCE: 3

Gln Gly Thr Leu Val Thr Val Ser Ala Ala Lys Thr Thr Pro Pro Ser
1               5                   10                  15

Val Tyr Pro Leu Ala Pro Gly Ser Ala Ala Gln Thr Asn Ser Met Val
                20                  25                  30

Thr Leu Gly Cys Leu Val Lys Gly Tyr Phe Pro Glu Pro Val Thr Val
            35                  40                  45

Thr Trp Asn Ser Gly Ser
        50

<210> SEQ ID NO 4
<211> LENGTH: 110
<212> TYPE: PRT
<213> ORGANISM: Mus musculus

<400> SEQUENCE: 4

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn His
                20                  25                  30

Trp Ile Gly Trp Val Lys Gln Arg Pro Gly His Gly Leu Glu Trp Ile
            35                  40                  45

Gly Asp Ile Tyr Pro Gly Ser Gly Tyr Thr Asn Tyr Asn Glu Lys Phe
        50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Ser Asp Tyr Tyr Gly Ser Trp Phe Ala Tyr Trp Gly
            100                 105                 110

<210> SEQ ID NO 5
<211> LENGTH: 110
<212> TYPE: PRT
<213> ORGANISM: Mus musculus

<400> SEQUENCE: 5

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
                20                  25                  30

Asp Gly Thr Thr Asp Leu Asn Trp Tyr Leu Gln Lys Pro Gly Gln Ser
            35                  40                  45
```

```
Pro Gln Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Glu Leu Gly Val Tyr Phe Cys Leu Gln Val
                85                  90                  95

Thr His Val Pro Trp Thr Phe Gly Gly Gly Thr Lys Leu Glu
                100                 105                 110

<210> SEQ ID NO 6
<211> LENGTH: 110
<212> TYPE: PRT
<213> ORGANISM: Mus musculus

<400> SEQUENCE: 6

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Lys Ser
                20                  25                  30

Asn Gly Asn Thr Tyr Leu Asn Trp Tyr Phe Gln Lys Pro Gly Gln Ser
            35                  40                  45

Pro Gln Leu Leu Ile Tyr Arg Val Ser Asn Arg Phe Ser Gly Val Leu
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Trp Thr Phe Gly Gly Gly Thr Lys Leu Glu
                100                 105                 110

<210> SEQ ID NO 7
<211> LENGTH: 110
<212> TYPE: PRT
<213> ORGANISM: Mus musculus

<400> SEQUENCE: 7

Asp Ala Val Met Thr Gln Thr Pro Leu Ser Leu Ser Val Ser Leu Gly
1               5                   10                  15

Asp Gln Ala Ser Ile Ser Cys Arg Ser Ser Gln Ser Leu Glu Asn Ser
                20                  25                  30

Asn Gly Asn Thr Tyr Leu Asn Trp Tyr Leu Gln Lys Pro Gly Gln Ser
            35                  40                  45

Pro Gln Leu Leu Ile Tyr Arg Val Ser Asn Arg Phe Ser Gly Val Leu
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Trp Thr Phe Gly Gly Gly Thr Lys Leu Glu
                100                 105                 110

<210> SEQ ID NO 8
<211> LENGTH: 110
<212> TYPE: PRT
<213> ORGANISM: Mus musculus

<400> SEQUENCE: 8

Gln Val Gln Leu Gln Gln Ser Gly Ala Glu Leu Val Arg Pro Gly Thr
```

```
                1               5                  10                  15
             Ser Val Lys Met Ser Cys Lys Ala Ala Gly Tyr Thr Phe Thr Lys Tyr
                              20                  25                  30

Trp Ile Gly Trp Val Lys Gln Arg Pro Gly His Gly Leu Glu Trp Ile
                          35                  40                  45

Gly Asp Ile Tyr Pro Gly Ser Gly Tyr Thr Asn Tyr Asn Glu Lys Phe
                      50                  55                  60

Lys Gly Lys Ala Lys Leu Thr Ala Asp Pro Ser Thr Thr Ala Tyr
              65                  70                  75                  80

Leu Gln Leu Ser Ser Leu Thr Ser Glu Asp Ser Ala Ile Tyr Tyr Cys
                              85                  90                  95

Ala Arg Ala Gly Asn Tyr Gly Ala Trp Phe Ala Tyr Trp Gly
                          100                 105                 110

<210> SEQ ID NO 9
<211> LENGTH: 109
<212> TYPE: PRT
<213> ORGANISM: Mus musculus

<400> SEQUENCE: 9

Gln Val Gln Leu Gln Gln Ser Gly Ala Glu Leu Val Arg Pro Gly Thr
              1               5                  10                  15

Ser Val Lys Met Ser Cys Lys Ala Ala Gly Tyr Thr Phe Thr Lys Tyr
                              20                  25                  30

Trp Ile Gly Trp Val Lys Gln Arg Pro Gly His Gly Leu Glu Trp Ile
                          35                  40                  45

Gly Asp Ile Tyr Pro Ala Gly Gly Tyr Thr Asn Tyr Asn Glu Lys Phe
                      50                  55                  60

Lys Gly Lys Ala Thr Leu Thr Ala Asp Thr Ser Ser Thr Ile Tyr
              65                  70                  75                  80

Met Gln Leu Ser Ser Leu Thr Ser Glu Asp Ser Ala Ile Tyr Tyr Cys
                              85                  90                  95

Cys Tyr Gly Tyr Gly Gly Ala Trp Phe Ser Tyr Trp Gly
                          100                 105

<210> SEQ ID NO 10
<211> LENGTH: 112
<212> TYPE: PRT
<213> ORGANISM: Mus musculus

<400> SEQUENCE: 10

Gln Val Gln Leu Gln Gln Ser Gly Ala Glu Leu Val Arg Pro Gly Thr
              1               5                  10                  15

Ser Val Lys Met Ser Cys Lys Ala Ala Gly Tyr Thr Phe Thr Asn Tyr
                              20                  25                  30

Trp Ile Gly Trp Val Lys Gln Arg Pro Gly His Asp Leu Glu Trp Ile
                          35                  40                  45

Gly Asp Ile Tyr Pro Gly Ser Gly Tyr Ala Tyr Tyr Asn Glu Lys Phe
                      50                  55                  60

Lys Gly Lys Ala Thr Leu Thr Ala Asp Thr Ser Ser Thr Ala Tyr
              65                  70                  75                  80

Met Gln Leu Ser Ser Leu Thr Ser Glu Asp Ser Ala Phe Tyr Tyr Cys
                              85                  90                  95

Val Arg Ser Tyr Phe Ala Asp Gly Pro Ala Trp Phe Ala Tyr Trp Gly
                          100                 105                 110
```

<210> SEQ ID NO 11
<211> LENGTH: 501
<212> TYPE: DNA
<213> ORGANISM: Mus musculus

<400> SEQUENCE: 11

| | | | | | |
|---|---|---|---|---|---|
| gatgctgtga | tgacccaaac | tccactctcc | ctgcctgtca | gtcttggaga | tcaagcctcc | 60 |
| atctcttgca | ggtctagtca | gagccttgaa | aacagtaatg | gaaacaccga | tttgaactgg | 120 |
| tacctccaga | aaccaggcca | gtctccacag | ctcctgatct | acagggtttc | caaccgattt | 180 |
| tctggggtcc | tagacaggtt | cagtggtagt | ggatcaggga | cagatttcac | actgaaaatc | 240 |
| agcagagtgg | aggctgagga | tttgggagtt | tatttctgcc | tccaagttac | acatgtcccg | 300 |
| tggacgttcg | gtggaggcac | caagctggac | atcaaacggg | ctgatgctgc | accaactgta | 360 |
| tccatcttcc | caccatccag | tgagcagtta | acatctggag | gtgcctcagt | cgtgtgcttc | 420 |
| ttgaacaact | tctaccccaa | agacatcaat | gtcaagtgga | agattgatgg | cagtgaacga | 480 |
| caaaatggcg | tcctgaacag | t | | | | 501 |

<210> SEQ ID NO 12
<211> LENGTH: 501
<212> TYPE: DNA
<213> ORGANISM: Mus musculus

<400> SEQUENCE: 12

| | | | | | |
|---|---|---|---|---|---|
| gatgctgtga | tgacccaaac | tccactctcc | ctgcctgtca | gtcttggaga | tcaagcctcc | 60 |
| atctcttgca | ggtctagtca | gagccttgaa | aacagtgatg | gaaccaccga | tttgaactgg | 120 |
| tacctccaga | aaccaggcca | gtctccacag | ctcctgatct | acagggtttc | caaccgattt | 180 |
| tctggggtcc | cagacaggtt | cagtggtagt | ggatcaggga | cagatttcac | actgaaaatc | 240 |
| agcagagtgg | aggctgagga | attgggagtt | tatttctgcc | ttcaagttac | acatgtcccg | 300 |
| tggacgttcg | gtggaggcac | caagctggaa | atcaaacggg | ctgatgctgc | accaactgta | 360 |
| tccatcttcc | caccatccag | tgagcagtta | acatctggag | gtgcctcagt | cgtgtgcttc | 420 |
| ttgaacaact | tctaccccaa | agacatcaat | gtcaagtgga | agattgatgg | cagtgaacga | 480 |
| caaaatggcg | tcctgaacag | t | | | | 501 |

<210> SEQ ID NO 13
<211> LENGTH: 501
<212> TYPE: DNA
<213> ORGANISM: Mus musculus

<400> SEQUENCE: 13

| | | | | | |
|---|---|---|---|---|---|
| gatgctgtga | tgacccaaac | tccactctcc | ctgcctgtca | gtcttggaga | tcaagcctcc | 60 |
| atctcttgca | ggtctagtca | gagccttgaa | aaaagtaatg | gaaacaccta | tttgaactgg | 120 |
| tatttccaga | aaccaggcca | gtctccacag | ctcctgatct | acagggtttc | caaccgattt | 180 |
| tctggggtcc | tagacaggtt | cactggtagt | ggatcaggga | cagatttcac | attgaaaatc | 240 |
| agcagagtgg | aggctgagga | tttgggagtt | tatttctgcc | tccaagttac | acatgtcccg | 300 |
| tggacgttcg | gtggaggcac | caagctggaa | atcaaacggg | ctgatgctgc | accaactgta | 360 |
| tccatcttcc | caccatccag | tgagcagtta | acatctggag | gtgcctcagt | cgtgtgcttc | 420 |
| ttgaacaact | tctaccccaa | agacatcaat | gtcaagtgga | agattgatgg | cagtgaacga | 480 |
| caaaatggcg | tcctgaacag | t | | | | 501 |

<210> SEQ ID NO 14

<211> LENGTH: 501
<212> TYPE: DNA
<213> ORGANISM: Mus musculus

<400> SEQUENCE: 14

| | | |
|---|---|---|
| gatgctgtga tgacccaaac tccactctcc ctgtctgtca gtcttggaga tcaagcctcc | 60 |
| atctcttgca ggtctagtca gagccttgaa acagtaatg gaaacaccta tttgaactgg | 120 |
| tacctccaga aaccaggcca gtctccacag ctcctgatct acagggtttc caaccgattt | 180 |
| tctggggtcc tagacaggtt cagtggtagt ggatcaggga cagatttcac actgaaaatc | 240 |
| agcagagtgg aggctgagga tttggagtt tatttctgcc tccaagttac acatgtcccg | 300 |
| tggacgttcg gtggaggcac caagctggaa atcaaacggg ctgatgctgc accaactgta | 360 |
| tccatcttcc caccatccag tgagcagtta acatctggag tgcctcagt cgtgtgcttc | 420 |
| ttgaacaact tctaccccaa agacatcaat gtcaagtgga agattgatgg cagtgaacga | 480 |
| caaaatggcg tcctgaacag t | 501 |

<210> SEQ ID NO 15
<211> LENGTH: 492
<212> TYPE: DNA
<213> ORGANISM: Mus musculus

<400> SEQUENCE: 15

| | | |
|---|---|---|
| caggtccagc tgcagcagtc tggagctgag ttggtaaggc ctgggacttc agtgaagatg | 60 |
| tcctgcaagg ctgctggata caccttcact aaccactgga taggttgggt aaagcagagg | 120 |
| cctggacatg gccttgagtg gattggagat atttaccctg gaagtggtta tactaactac | 180 |
| aatgagaagt tcaagggcaa ggccacactg actgcagaca catcctccag cacagcctac | 240 |
| atgcagctca gcagcctgac atctgaggac tctgccatct attactgtgc aagatccgat | 300 |
| tactacggct cctggtttgc ttactgggc caagggactc tggtcactgt ctctgcagcc | 360 |
| aaaacgacac ccccatctgt ctatccactg gcccctggat ctgctgccca aactaactcc | 420 |
| atggtgaccc tgggatgcct ggtcaagggc tatttccctg agccagtgac agtgacctgg | 480 |
| aactctggat cc | 492 |

<210> SEQ ID NO 16
<211> LENGTH: 492
<212> TYPE: DNA
<213> ORGANISM: Mus musculus

<400> SEQUENCE: 16

| | | |
|---|---|---|
| caggtccagc tgcagcagtc tggagctgag ctggtaaggc ctgggacttc agtgaagatg | 60 |
| tcctgcaagg ctgctggata caccttcact aaatactgga taggttgggt aaagcagagg | 120 |
| cctggacatg gccttgagtg gattggagat atttaccctg gaagtggtta tactaactac | 180 |
| aatgagaaat tcaagggcaa ggccaaactg actgcagacc cttcctccac cacagcctac | 240 |
| ctgcagctca gcagcctgac atctgaggac tctgccatct attactgtgc aagagcggga | 300 |
| aattacggcg cctggtttgc ttactggggt caagggactc tggtcactgt ctctgcagcc | 360 |
| aaaacgacac ccccatctgt ctatccactg gcccctggat ctgctgccca aactaactcc | 420 |
| atggtgaccc tgggatgcct ggtcaagggc tatttccctg agccagtgac agtgacctgg | 480 |
| aactctggat cc | 492 |

<210> SEQ ID NO 17
<211> LENGTH: 489

```
<212> TYPE: DNA
<213> ORGANISM: Mus musculus

<400> SEQUENCE: 17
caggtccagc tgcagcagtc tggagctgag ctggtaaggc ctgggacttc agtgaagatg      60
tcctgcaagg ctgctggata caccttcact aagtattgga taggttgggt taagcagagg     120
cctggacatg gccttgagtg gattggagat atttaccctg caggtggtta tactaactac     180
aatgagaagt tcaagggcaa ggccacactg actgcagaca catcctccag cacaatctac     240
atgcagctca gcagcctgac atctgaggac tctgccatct attactgttg ctatggttac     300
ggcgggcct ggttttctta ctggggccaa gggactctgg tcactgtctc tgcagccaaa     360
acgacacccc catctgtcta tccactggcc cctggatctg ctgcccaaac taactccatg     420
gtgaccctgg gatgcctggt caagggctat ttccctgagc cagtgacagt gacctggaac     480
tctggatcc                                                             489

<210> SEQ ID NO 18
<211> LENGTH: 498
<212> TYPE: DNA
<213> ORGANISM: Mus musculus

<400> SEQUENCE: 18
caggtccaac tgcagcagtc tggagctgag ctggtaaggc ctgggacttc agtgaagatg      60
tcctgcaagg ctgctggata caccttcact aactactgga taggttgggt aaagcagagg     120
cctggacatg accttgagtg gattggagat atttaccctg gaagtggtta tgcttactac     180
aatgagaagt tcaagggcaa ggccacactg actgcagaca catcctccag cacagcctac     240
atgcagctca gcagcctgac atctgaggac tctgccttct attactgtgt aagatcctac     300
ttcgctgatg gccggcctg gtttgcttac tggggccaag ggactctggt cactgtctct     360
gcagccaaaa cgacaccccc atctgtctat ccactggccc ctggatctgc tgcccaaact     420
aactccatgg tgaccctggg atgcctggtc aagggctatt tccctgagcc agtgacagtg     480
acctggaact ctggatcc                                                   498

<210> SEQ ID NO 19
<211> LENGTH: 167
<212> TYPE: PRT
<213> ORGANISM: Mus musculus

<400> SEQUENCE: 19

Asp Ala Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Glu Asn Ser
             20                  25                  30

Asn Gly Asn Thr Asp Leu Asn Trp Tyr Leu Gln Lys Pro Gly Gln Ser
         35                  40                  45

Pro Gln Leu Leu Ile Tyr Arg Val Ser Asn Arg Phe Ser Gly Val Leu
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Leu Gln Val
                 85                  90                  95

Thr His Val Pro Trp Thr Phe Gly Gly Gly Thr Lys Leu Asp Ile Lys
            100                 105                 110

Arg Ala Asp Ala Ala Pro Thr Val Ser Ile Phe Pro Pro Ser Ser Glu
```

-continued

```
                115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser
            165

<210> SEQ ID NO 20
<211> LENGTH: 167
<212> TYPE: PRT
<213> ORGANISM: Mus musculus

<400> SEQUENCE: 20

Asp Ala Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Glu Asn Ser
             20                  25                  30

Asp Gly Thr Thr Asp Leu Asn Trp Tyr Leu Gln Lys Pro Gly Gln Ser
         35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Glu Leu Gly Val Tyr Phe Cys Leu Gln Val
                 85                  90                  95

Thr His Val Pro Trp Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser
            165

<210> SEQ ID NO 21
<211> LENGTH: 167
<212> TYPE: PRT
<213> ORGANISM: Mus musculus

<400> SEQUENCE: 21

Asp Ala Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Glu Lys Ser
             20                  25                  30

Asn Gly Asn Thr Tyr Leu Asn Trp Tyr Phe Gln Lys Pro Gly Gln Ser
         35                  40                  45

Pro Gln Leu Leu Ile Tyr Arg Val Ser Asn Arg Phe Ser Gly Val Leu
    50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Phe Cys Leu Gln Val
                 85                  90                  95

Thr His Val Pro Trp Thr Phe Gly Gly Gly Thr Lys Leu Glu Ile Lys
```

```
                  100                 105                 110
Arg Ala Asp Ala Ala Pro Thr Val Ser Ile Phe Pro Ser Ser Glu
            115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser
                165

<210> SEQ ID NO 22
<211> LENGTH: 167
<212> TYPE: PRT
<213> ORGANISM: Mus musculus

<400> SEQUENCE: 22

Asp Ala Val Met Thr Gln Thr Pro Leu Ser Leu Ser Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Trp Thr Phe Gly Gly Gly Thr Lys Leu Glu Ile Lys
                100                 105                 110

Arg Ala Asp Ala Ala Pro Thr Val Ser Ile Phe Pro Ser Ser Glu
            115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser
                165

<210> SEQ ID NO 23
<211> LENGTH: 164
<212> TYPE: PRT
<213> ORGANISM: Mus musculus

<400> SEQUENCE: 23

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn His
            20                  25                  30

Trp Ile Gly Trp Val Lys Gln Arg Pro Gly His Gly Leu Glu Trp Ile
        35                  40                  45

Gly Asp Ile Tyr Pro Gly Ser Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Ile Tyr Tyr Cys
```

```
                     85                  90                  95
Ala Arg Ser Asp Tyr Tyr Gly Ser Trp Phe Ala Tyr Trp Gly Gln Gly
            100                 105                 110

Thr Leu Val Thr Val Ser Ala Ala Lys Thr Thr Pro Pro Ser Val Tyr
            115                 120                 125

Pro Leu Ala Pro Gly Ser Ala Ala Gln Thr Asn Ser Met Val Thr Leu
            130                 135                 140

Gly Cys Leu Val Lys Gly Tyr Phe Pro Glu Pro Val Thr Val Thr Trp
145                 150                 155                 160

Asn Ser Gly Ser

<210> SEQ ID NO 24
<211> LENGTH: 164
<212> TYPE: PRT
<213> ORGANISM: Mus musculus

<400> SEQUENCE: 24

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Lys Tyr
            20                  25                  30

Trp Ile Gly Trp Val Lys Gln Arg Pro Gly His Gly Leu Glu Trp Ile
        35                  40                  45

Gly Asp Ile Tyr Pro Gly Ser Gly Tyr Thr Asn Tyr Asn Glu Lys Phe
    50                  55                  60

Lys Gly Lys Ala Lys Leu Thr Ala Asp Pro Ser Ser Thr Thr Ala Tyr
65                  70                  75                  80

Leu Gln Leu Ser Ser Leu Thr Ser Glu Asp Ser Ala Ile Tyr Tyr Cys
                85                  90                  95

Ala Arg Ala Gly Asn Tyr Gly Ala Trp Phe Ala Tyr Trp Gly Gln Gly
            100                 105                 110

Thr Leu Val Thr Val Ser Ala Ala Lys Thr Thr Pro Pro Ser Val Tyr
            115                 120                 125

Pro Leu Ala Pro Gly Ser Ala Ala Gln Thr Asn Ser Met Val Thr Leu
            130                 135                 140

Gly Cys Leu Val Lys Gly Tyr Phe Pro Glu Pro Val Thr Val Thr Trp
145                 150                 155                 160

Asn Ser Gly Ser

<210> SEQ ID NO 25
<211> LENGTH: 163
<212> TYPE: PRT
<213> ORGANISM: Mus musculus

<400> SEQUENCE: 25

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Lys Tyr
            20                  25                  30

Trp Ile Gly Trp Val Lys Gln Arg Pro Gly His Gly Leu Glu Trp Ile
        35                  40                  45

Gly Asp Ile Tyr Pro Ala Gly Gly Tyr Thr Asn Tyr Asn Glu Lys Phe
    50                  55                  60

Lys Gly Lys Ala Thr Leu Thr Ala Asp Thr Ser Ser Ser Thr Ile Tyr
65                  70                  75                  80
```

```
Met Gln Leu Ser Ser Leu Thr Ser Glu Asp Ser Ala Ile Tyr Tyr Cys
                85                  90                  95

Cys Tyr Gly Tyr Gly Gly Ala Trp Phe Ser Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser

<210> SEQ ID NO 26
<211> LENGTH: 166
<212> TYPE: PRT
<213> ORGANISM: Mus musculus

<400> SEQUENCE: 26

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Asp Leu Glu Trp Ile
        35                  40                  45

Gly Asp Ile Tyr Pro Gly Ser Gly Tyr Ala Tyr Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Phe Tyr Tyr Cys
                85                  90                  95

Val Arg Ser Tyr Phe Ala Asp Gly Pro Ala Trp Phe Ala Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser
                165

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: acetyllysine

<400> SEQUENCE: 27

Ser Gly Arg Gly Lys Xaa Gln Gly Gly Lys Cys
1               5                   10

<210> SEQ ID NO 28
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: acetyllysine

<400> SEQUENCE: 28

Pro Glu Pro Ala Lys Xaa Ser Ala Pro Ala Cys
  1               5                  10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: acetyllysine

<400> SEQUENCE: 29

Pro Ala Pro Lys Lys Xaa Gly Ser Lys Lys Cys
  1               5                  10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: acetyllysine

<400> SEQUENCE: 30

Lys Lys Gly Ser Lys Xaa Lys Ala Val Thr Cys
  1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: acetyllysine

<400> SEQUENCE: 31

Thr Ala Arg Lys Xaa Ser Thr Gly Gly Lys Ala Cys
  1               5                  10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (6)
<223> OTHER INFORMATION: acetyllysine

<400> SEQUENCE: 32

Ser Thr Gly Gly Lys Xaa Ala Pro Arg Lys Cys
 1               5                  10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: acetyllysine

<400> SEQUENCE: 33

Lys Ala Pro Arg Lys Xaa Gln Leu Ala Thr Cys
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: acetyllysine

<400> SEQUENCE: 34

Leu Ala Thr Lys Xaa Ala Ala Arg Lys Ser Ala Cys
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: acetyllysine

<400> SEQUENCE: 35

Ser Gly Arg Gly Lys Xaa Gly Gly Lys Gly Leu Cys
 1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: acetyllysine

<400> SEQUENCE: 36

Lys Gly Gly Ala Lys Xaa Arg His Arg Lys Val Cys
 1               5                  10
```

-continued

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Gly Arg Gly Lys Gly Gly Lys Gly Leu Gly Lys Gly Gly Ala Lys
 1               5                  10                  15

Arg His Arg Lys Val Cys
            20

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: acetyllysine

<400> SEQUENCE: 38

Ser Pro Gln Pro Lys Lys Xaa Lys Pro Leu Cys
 1               5                  10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: acetyllysine

<400> SEQUENCE: 39

His Leu Lys Ser Lys Lys Xaa Gly Gln Ser Cys
 1               5                  10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: acetyllysine

<400> SEQUENCE: 40

Thr Ser Arg His Lys Lys Xaa Leu Met Phe Cys
 1               5                  10

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic

```
                                    -continued
    primer

<400> SEQUENCE: 41
actgttcagg acgccatttt gtcgttcact                                              30

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggatccagag ttccaggtca ctgt                                                    24
```

ACETYLLYSINE-RECOGNIZING MONOCLONAL ANTIBODY AND PROCESS FOR PRODUCING THE SAME

TECHNICAL FIELD

The present invention relates to a novel monoclonal antibody and a method for producing the same. Specifically, the present invention relates to a monoclonal antibody capable of recognizing an $N^\epsilon$-acetyllysine residue in a protein without depending on the type of an adjacent amino acid, and a method for producing the same.

BACKGROUND ART

In recent years, it has become apparent that an $N^\epsilon$-acetylation of the lysine residue in N-terminal region of a core histone plays an important role in the control of gene expression of eukaryotes. The enzyme of a histone acetyltransferase responsible for the acetylation and the enzyme of a histone deacetylase responsible for deacetylation were cloned in 1996 for the first time, and after that, a plurality of molecules having similar activities have been found. In recent years, furthermore, beside histone, it has been found that various kinds of non-histone proteins such as p53, TCF, and HMG-1 could be acetylated. It has been pointed out that the acetylation may be post-translation modification that plays various roles as equally as phosphorylation.

To search for an unknown novel acetylation protein as described above, there is no need to discuss the usefulness of a probe molecule that recognizes an $N^\epsilon$-acetyllysine residue specifically and irrespectively of the adjacent amino acid. An antibody has been considered as the most suitable molecule for the object. However, the antibody capable of recognizing acetyllysine under various conditions irrespective of the types of the adjacent amino acids has been hardly reported.

DISCLOSURE OF THE INVENTION

The present invention has been completed in view of the present circumstances and aims to provide an $N^\epsilon$-acetyllysine-recognizing anti-acetyllysine monoclonal antibody which does not particularly depend on the types of the adjacent amino acids and is capable of allowing wide varieties of adjacent amino acids.

The present inventors have been dedicated to the study of solving the above problems and finally attained success to produce an anti-acetyllysine monoclonal antibody capable of allowing wide varieties of adjacent amino acids. Furthermore, the present invention has been completed by determining cDNA sequences of variable regions of the respective monoclonal antibodies being produced to make it clear that the produced antibodies have their characterized structures which are similar to each other.

In other words, the present invention relates to a monoclonal antibody that recognizes $N^\epsilon$-acetyllysine. In particular, the present invention relates to a monoclonal antibody which does not particularly depend on the types of the adjacent amino acids and is capable of allowing wide varieties of adjacent amino acids.

More specifically, the present invention relates to a monoclonal antibody comprising: (1) a light chain comprising a constant region having the amino acid sequence represented by SEQ ID NO.: 1 and a variable region having the amino acid sequence represented by SEQ ID NO.: 2, or an amino acid sequence derived from this amino acid sequence by deletion, substitution or addition of one or several amino acids; (2) a heavy chain comprising a constant region having the amino acid sequence represented by SEQ ID NO.: 3 and a variable region having the amino acid sequence represented by SEQ ID NO.: 4, or an amino acid sequence derived from this amino acid sequence by deletion, substitution or addition of one or several amino acids.

Furthermore, the present invention relates to a method for producing the monoclonal antibody characterized in that the chemically acetylated protein being is used as an antigen.

BRIEF DESCRIPTION OF THE DRAWINGS

FIG. 4 shows the results of comparing between amino acid sequences of the variable regions of heavy chain (SEQ ID NOS 23–26, respectively in order of appearance) and light chain (SEQ ID NOS 19–22, respectively in order of appearance) of four kinds of anti-acetyllysine monoclonal antibodies of the present invention.

BRIEF MODE FOR CARRYING OUT THE INVENTION

Figure 1:
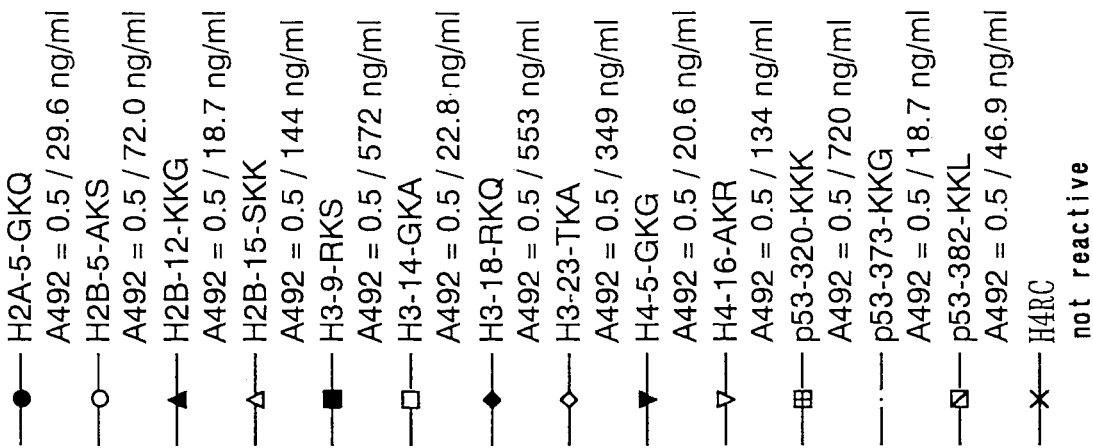
FIG. 1 shows the comparison (ELISA method) between the reactivities of four kinds of anti-acetyllysine monoclonal antibodies of the present invention with respect to various acetyllysine-containing peptides.
Figure 1:
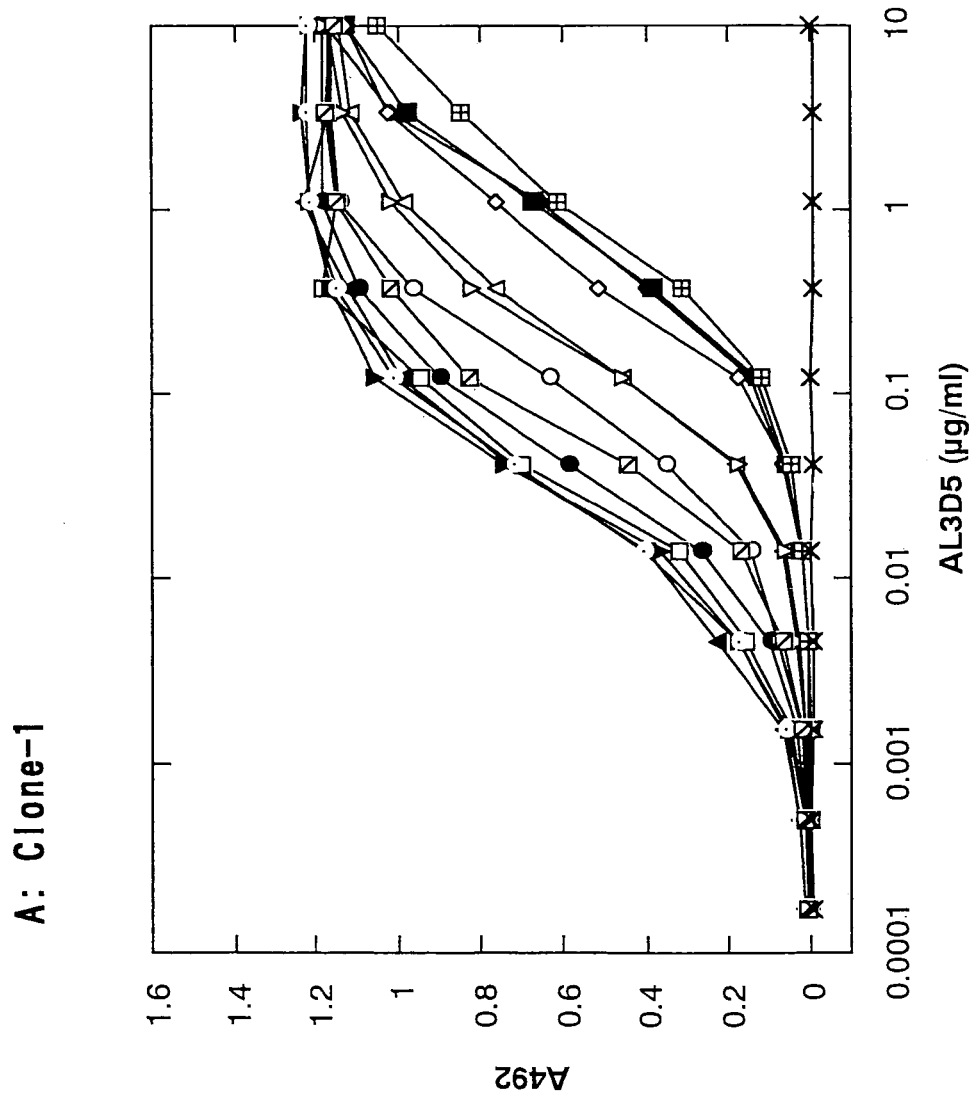
Figure 1:
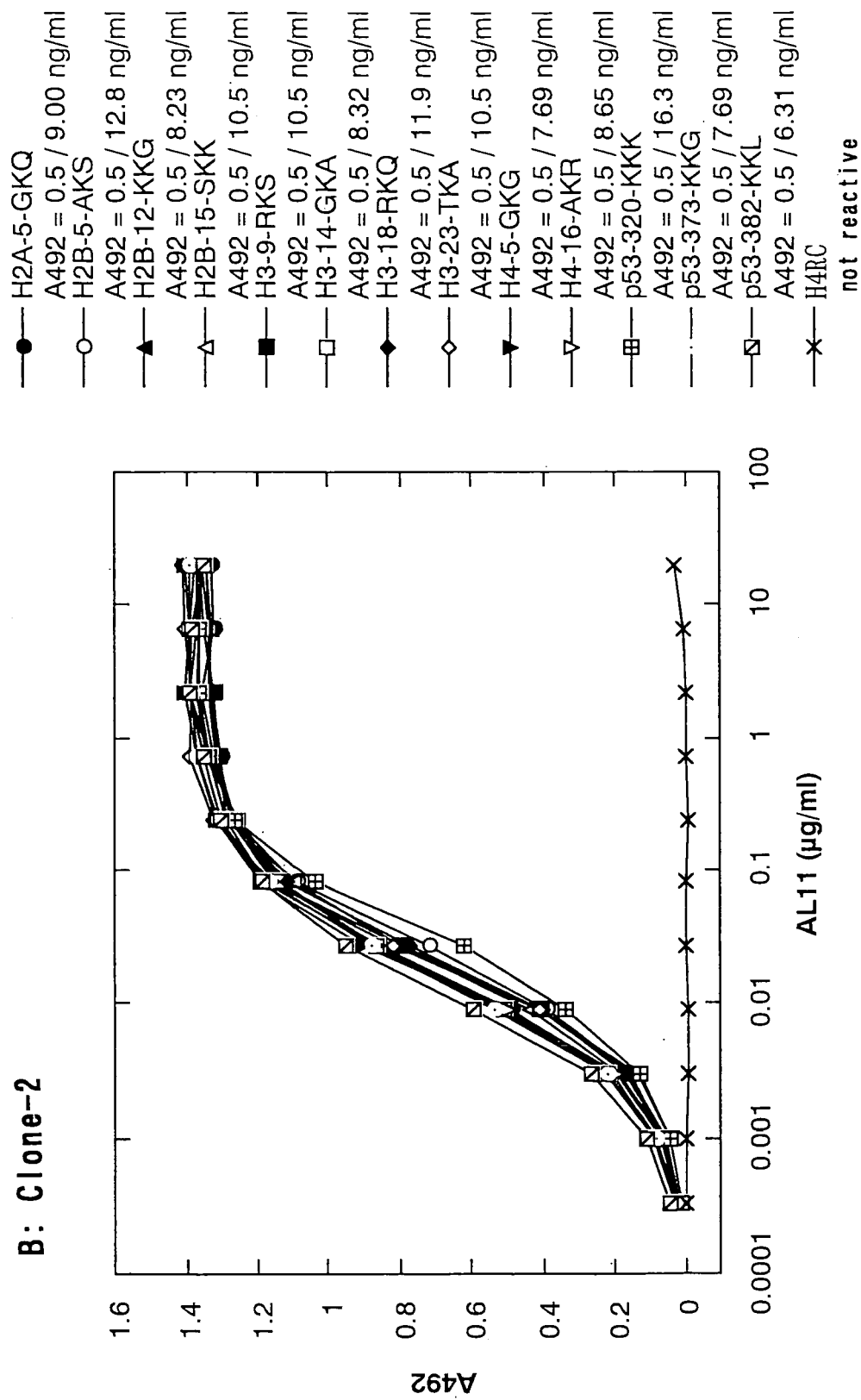
Figure 1:
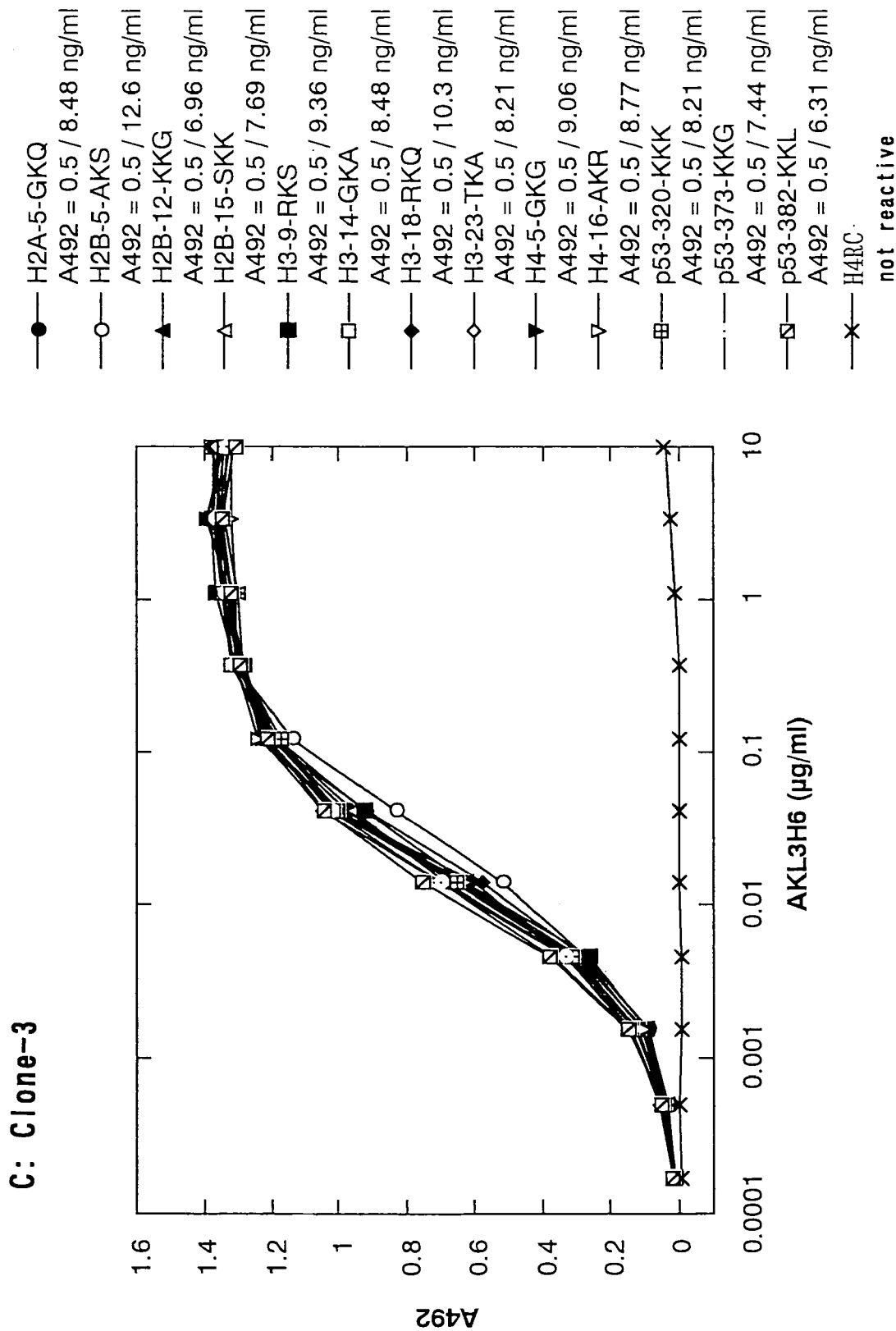
Figure 1:
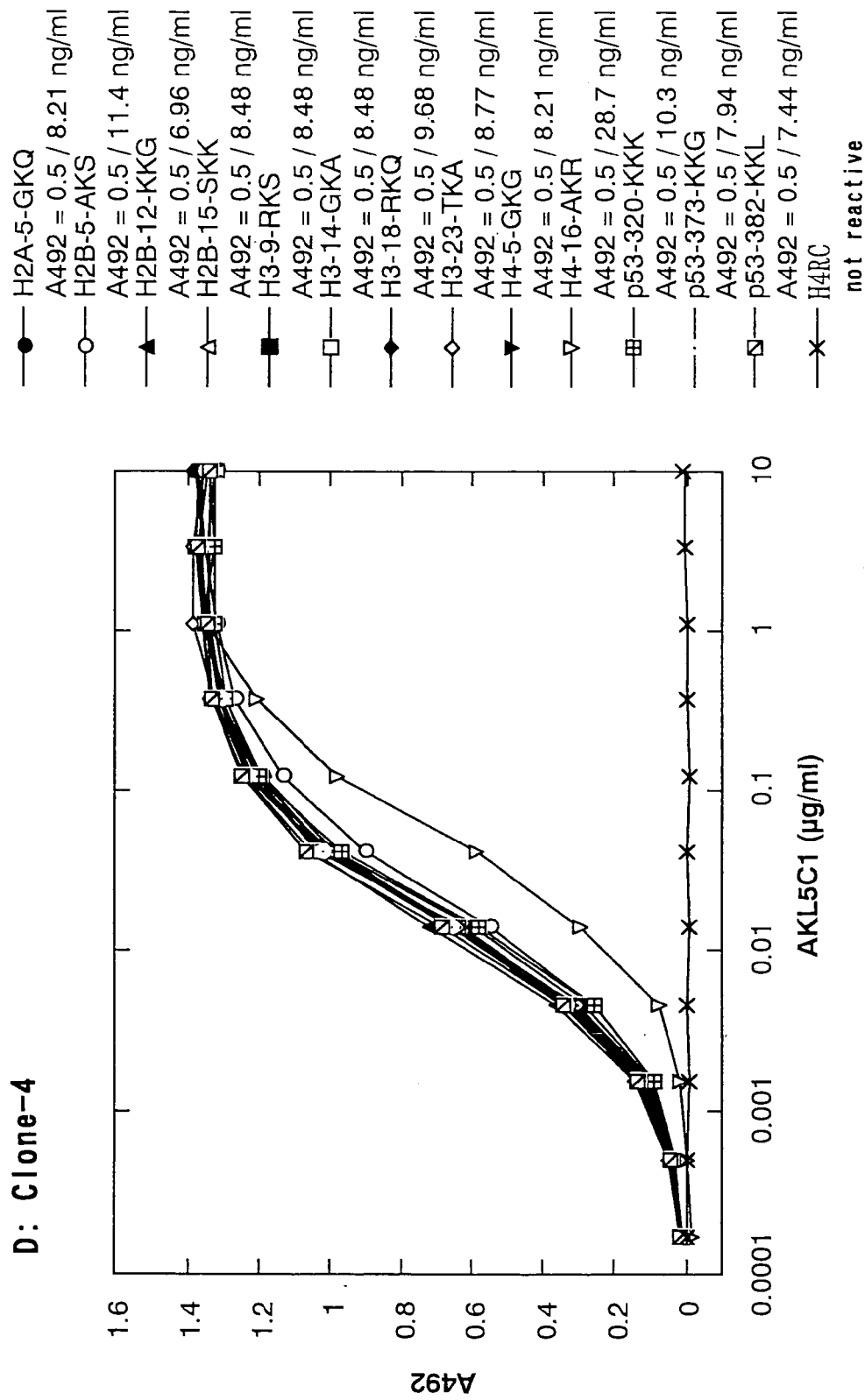

In the monoclonal antibody of the present invention, the variable region of the light chain having the amino acid sequence, represented by SEQ ID NO.: 2, where one or several amino acids are substituted includes, for example, an amino acid sequence of SEQ ID NO.: 5, SEQ ID NO.: 6, or SEQ ID NO.: 7.

Furthermore, in the monoclonal antibody of the present invention, the variable region of a heavy chain, having the amino acid sequence represented by SEQ ID NO.: 4, where one or several amino acids are substituted, includes, for example, an amino acid sequence represented by SEQ ID NO.: 8; where one or several amino acids are deleted, includes, for example, an amino acids sequence, represented by SEQ ID NO.: 9; where one or several amino acids are added, includes, for example, an amino acid sequence represented by SEQ ID NO.: 10, respectively.

The monoclonal antibodies of the present invention are antibodies that recognize $N^\epsilon$-acetyllysine and have the properties of allowing wide varieties of adjacent amino acids without depending on the types of their adjacent amino acids when recognizing $N^\epsilon$-acetyllysine residue existing in protein. These antibodies can be prepared by using various kinds of acetyllysine-containing molecules as antigens. The antibody having particularly excellent properties is obtained by a method of preparation in which a chemically acetylated protein having a plurality of lysine residues is used as an antigen.

The antibodies of the present invention include those obtained by binding synthetic peptides containing acetyllysine with carrier proteins such as purple-limpet hemocya nin, or those produced by antibody-producing immortalized cells, obtained by immobilizing the antibody-producing cells such as spleen cells are fused with myeloma cells or the like, where the antibody-producing cells are obtained by immunizing an animal such as a mouse using a protein in which a plurality of lysine residues are chemically acetylated, for example purple-limpet hemocyanin acetylated by acetic anhydride, as an antibody.

Among the above antigen molecules, A method using a protein containing a plurality of lysine residues in the molecule thereof is chemically acetylated, is more preferable than a method using a peptide containing a single lysine residue as an antigen. Therefore, it is easily thinkable that using a mixture of various kinds of acetyllysine-containing peptides is preferable for obtaining excellent antibodies.

Alternatively, antibody-producing cells can be obtained by various methods in which antibody libraries displayed on phages are screened by means of their affinities with antigens.

For obtaining such antibody-producing immortalized cells, all the monoclonal antibody producing technologies, which have been conventionally used, and which will be newly developed in future, can be used.

The screening of antibody-producing cells can be performed by selecting a clone that produces an antibody allowing adjacent amino acids as much as possible by using a protein, different from an antigen in which a plurality of lysine residues are acetylated, such as acetylated bovine serum albumin or a acetyllysine-containing peptide having various kinds of adjacent amino acids. In addition, the produced antibody molecules can be purified by an affinity column in which acetyllysine is immobilized or an affinity column using protein A.

It can be detected whether the produced antibody corresponds to the antibody of the present invention by analyzing a DNA sequence of the variable region of the antibody gene in the antibody-producing immobilized cell, and translating it into a protein, and determined by whether it has a high similarity of the sequential characteristics of the protein with the above sequence or not.

Furthermore, the present invention provides a gene, preferably DNA, which encodes a monoclonal antibody that recognizes $N^\epsilon$-acetyllysine of the present invention, which has been mentioned above. Examples of the DNA of the present invention are shown in SEQ ID Nos. 11 to 18 in the sequence table. SEQ ID Nos. 11 to 14 are related to light chains, and SEQ ID Nos. 15 to 18 are related to heavy chains, respectively. The DNA of the present invention includes complement chains thereof, or the base sequences capable of hybridizing with these base sequences under stringent conditions.

In the monoclonal antibodies of the present invention, as sensitized animals, various species of mammals such as mice, rats, rabbits, and dogs, and birds such as chickens can be used. In addition, it is also possible to make chimeric antibodies or human-type antibodies using variable regions and/or a hypervariable region of the monoclonal antibody of the present invention.

EXAMPLES

Hereinafter, the present invention will be explained in details with reference to the examples. However, the present invention is not limited to these examples at all.

Example 1

Preparation of Anti-$N^\epsilon$-acetyllysine Monoclonal Antibody

The anti-$N^\epsilon$-acetyllysine monoclonal antibody was prepared with a combination of three kinds of immunological antigens and screening antigens as described in Table 1. Furthermore, the acetylation of bovine serum albumin and purple-limpet hemocyanin was performed using acetic anhydride by the following method. 10 mg of protein was dissolved in 1 ml of a borate buffer (20 mM $Na_2B_4O_7$, pH 9.3), and then 250 μmol of acetic anhydride (about 22.6 μl) and 500 μl of 1M NaOH were added therein while cooling with ice, followed by incubating for 30 minutes with stirring occasionally. After the reaction, a solvent was changed using a G-25 gel filtration (PD-10, Pharmacia Co., Ltd.) and a phosphate buffer solution (PBS) of acetylated protein was obtained.

TABLE 1

| | Immunological antigen | Screening antigen |
|---|---|---|
| Case 1 | Conjugate of acetylated N-terminal peptide of histone H4 with purple-limpet hemocyanin | Acetylated N-terminal peptide of histone H3 |
| Case 2 | Conjugate of acetylated N-terminal peptide of histone H4 with purple-limpet hemocyanin | Bovine serum albumin being acetylated with acetic anhydride |
| Case 3 | Purple-limpet hemocyanin being acetylated with acetic anhydride | Bovine serum albumin being acetylated with acetic anhydride, and acetylated peptide |

The immunization was performed on female Balb/c mice every week for three weeks intraperitoneally, using Freund's complete adjuvant at the first time, and Freund's incomplete adjuvant at the second and third times. The amount of immunization is 0.1 mg/mouse.

From the mouse on which the immunization was completed, hybridoma that produces an anti-acetyllysine monoclonal antibody was cloned using the conventional method. As a result, Clone-1 from Case 1, Clone-2 from Case 2, and Clone-3 and Clone-4 from Case 3 were established. Using various kinds of acetyllysine-containing peptides covalently bonded to an ELISA plate (Iwaki Glass Co., Ltd., AquaBind Plate) through their C-terminal cysteine, the results of comparing reactivities thereon are shown in FIG. 1. In FIG. 1, "A" presents the results of Clone-1, "B" represents those of Clone-2, "C" represents those of Clone-3, and "D" represents those of Clone-4, respectively. The right side of each graph denotes the concentration of each antibody at the time of providing an absorbance of 0.5. In addition, a list of peptides used in the figure is as shown in Table 2. As shown in FIG. 1, it was found that each of the antibodies of Clone-1 to Clone-4 showed the binding reactivity to acetyllysine under the conditions in which various kinds of adjacent amino acids were present. From this experiment, three clones, Clone-2 to Clone 4, showed their reactivities at almost same level as the respective peptides investigated at this time and it was found that they accept adjacent amino acids widely.

In addition, as a result of determining isotypes of the respective antibodies, it was confirmed that all of them were Ig G1κ.

TABLE 2

| Name of Peptides | Amino Acid Sequence | |
|---|---|---|
| H2A-5-GKQ | SGRGK(Ac)QGGKC | (SEQ ID NO: 27) |
| H2B-5-AKS | PEPAK(Ac)SAPAC | (SEQ ID NO: 28) |
| H2B-12-KKG | PAPKK(Ac)GSKKC | (SEQ ID NO: 29) |
| H2B-15-SKK | KKGSK(Ac)KAVTC | (SEQ ID NO: 30) |
| H3-9-RKS | TARK(Ac)STGGKAC | (SEQ ID NO: 31) |
| H3-14-GKA | STGGK(Ac)APRKC | (SEQ ID NO: 32) |
| H3-18-RKQ | KAPRK(Ac)QLATC | (SEQ ID NO: 33) |
| H3-23-TKA | LATK(Ac)AARKSAC | (SEQ ID NO: 34) |
| H4-5-GKG | SGRGK(Ac)GGKGLC | (SEQ ID NO: 35) |
| H4-16-AKR | KGGAK(Ac)RHRKVC | (SEQ ID NO: 36) |
| H4RC | SGRGKGGKGLGKGGAKRHRKVC | (SEQ ID NO: 37) |
| p53-320 | SPQPKK(Ac)KPLC | (SEQ ID NO: 38) |
| p53-373 | HLKSKK(Ac)GQSC | (SEQ ID NO: 39) |
| p53-382 | TSRHKK(A)LMFC | (SEQ ID NO: 40) |

Numbers added on the right side of each name denotes the position of the corresponding acetyllysine residue in each protein. H4RC represents a non-acetylated peptide. In addition, amino acid sequences in the table are represented by means of a one-character notation.

Example 2

Detection of Acetylated Protein by Western Blotting Method

Figure 2:
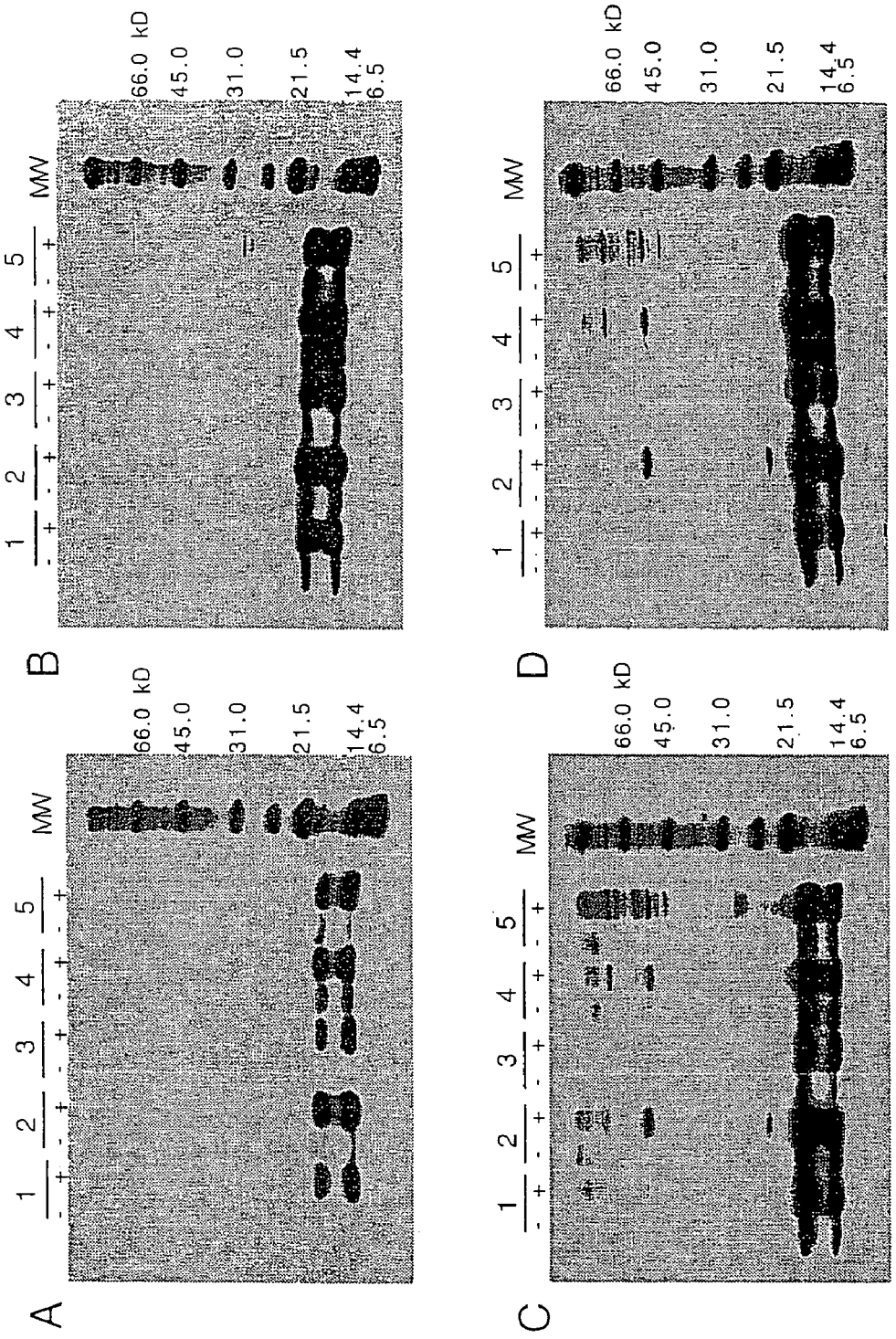
FIG. 2 shows the results of detecting acetylated proteins in the total cell lysates of various kinds of cells using four kinds of anti-acetyllysine monoclonal antibodies.

Five types of cells, B16/BL6, MOLT-4F, HeLa-S3, COS-1, and COS-7 were treated with, 1 μM of histone-deacetylase inhibitor, CHAP31, for 24 hours, and then cell lysates were prepared and developed on an electrophoresis, followed by detecting acetylated proteins using the above four antibodies as primary antibodies. The results were shown in FIG. 2. In FIGS. 2, A, B, C, and D indicate the results of the detections using Clone-1, Clone-2, Clone-3, and Clone-4, respectively. The concentration of the primary antibodies used for the Western blotting were 107 ng/ml, 65.7 ng/ml, 258 ng/ml, and 158 ng/ml, respectively, and each of these concentration provide the same reactivity (A492=1) in ELISA where acetylated bovine serum albumin was immobilized. The total cell lysates were prepared from the cells (+) after subjecting each cell in the 1 μM CHAP31 treatment for 24 hours or the cells (−) without the treatment. In each lane, 20 μg of protein was loaded. Five types of cells being used were 1: B16/BL6, 2: MOLT-4F, 3: HeLa-S3, 4: COS-1, and 5: COS-7, respectively.

As shown in FIG. 2, the Clone-1 antibody prepared in Case 1 of Example 1 detected only the acetylation of histone increased by CHAP31. In addition, the Clone-2 antibody prepared in Case 2 detected several proteins other than histone, but had an insufficient reactivity to the others. On the other hand, the Clone-3 and Clone-4 antibodies prepared in Case 3 strongly detected acetylated proteins on the position around 50 kDa other than histone in MOT-4F, COS-1, and COS-7 cells. Furthermore, it was found that they can detect a plurality of proteins around 20 kDa and high-molecular portions in the MOLT-4F cell, and much more acetylated proteins in the COS-7 cells. From these results, it was confirmed that in the detection of the acetylated non-histone protein by the Western blotting method, Clone-3 and Clone-4 prepared by using acetylated purple-limpet hemocyanin as an antigen are particularly excellent. In other words, it was found that for preparing the antibody capable of accepting wide varieties of adjacent amino acids of acetyllysine, the use of a molecule, of which a plurality of lysine residues in the protein was acetylated, such as the acetylated purple-limpet hemocyanin, as an antibody is preferable.

Example 3

Confirmation of Specificity to $N^\epsilon$-Acetyllysine

Figure 3:
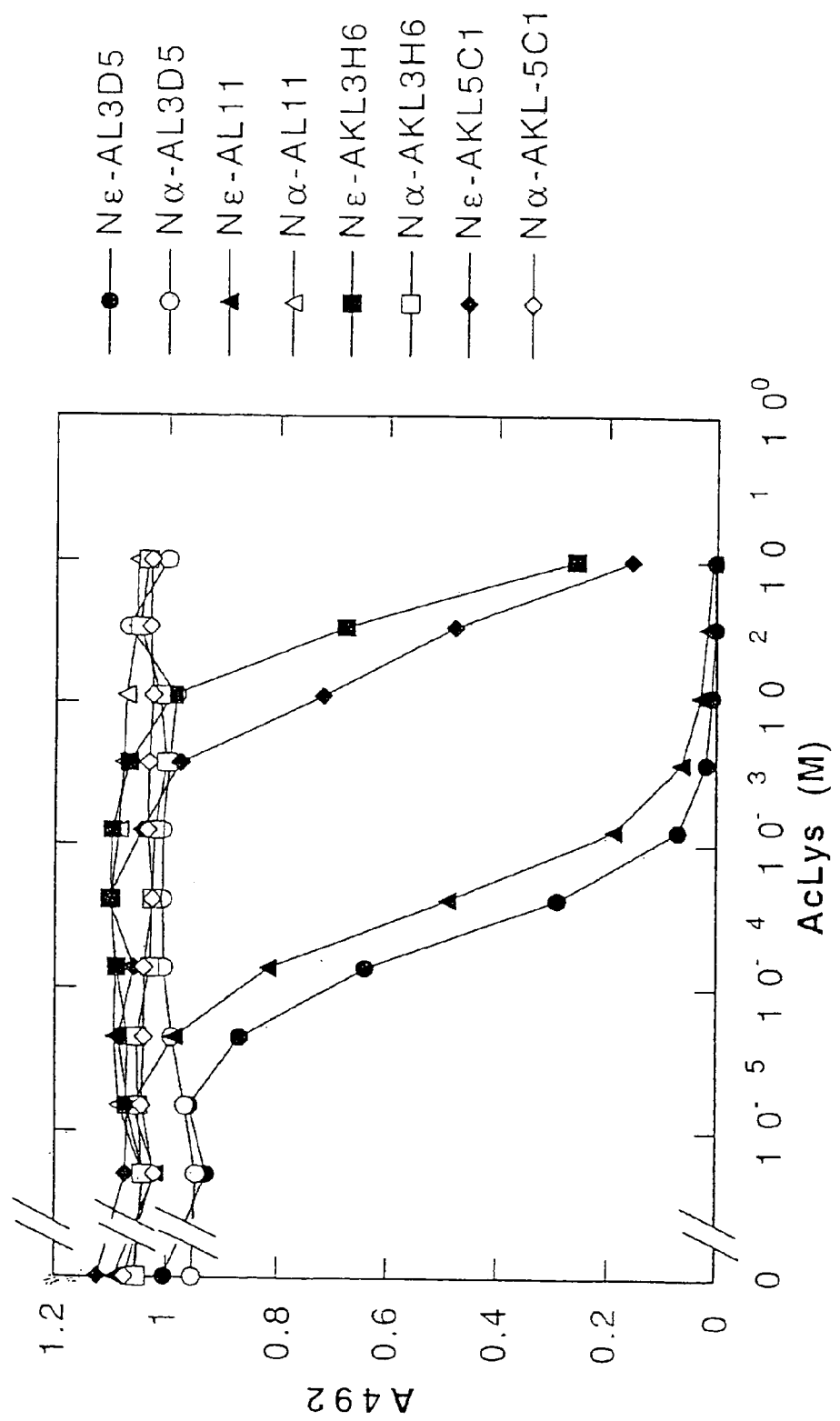
FIG. 3 shows the results of investigating whether the ELISA reactivities of four kinds of anti-acetyllysine monoclonal antibodies of the present invention are competed with $N^\epsilon$-acetyllysine and $N^\alpha$-acetyllysine.

To confirm that the prepared antibody was specifically reacting with $N^\epsilon$-acetylated lysine, acetylated bovine serum albumin was immobilized on an ELISA plate and investigated whether the reactivities of the respective antibodies to the ELISA were competed with $N^\epsilon$-acetyllysine and $N^\alpha$-acetyllysine. That is, the ELISA plate immobilized with a phosphate buffer solution (50 μl) of 1 μg/ml acetylated bovine serum albumin at 4° C. overnight was used, and then the inhibitions by $N^\epsilon$-acetyllysine and $N^\alpha$-acetyllysine were investigated under the conditions on which 1 μg/ml of each antibody was reacted. The results are shown in FIG. 3. In the figure, ●, ▲, ■, and ◆ show the results of the inhibitions by $N^\epsilon$-acetyllysine and ○, △, □, and ◇ show the results of the inhibitions by $N^\alpha$-acetyllysine, respectively. Furthermore, ● and ○ are results of the case using Clone-1 (AL3D5); ▲ and △ are results of the case using Clone-2 (AL11); ■ and □ are results of the case using Clone-3 (AKL3H6); and ◆ and ◇ are results of the case using Clone-4 (AKL5C1), respectively.

As is obvious from FIG. 3, the reactivity of each antibody of Clone-1 to Clone-4 decreased as being competed with $N^\epsilon$-acetyllysine, but not competed with $N^\alpha$-acetyllysine. Accordingly, it has become obvious that these antibodies specifically react with $N^\epsilon$-acetyllysine.

Example 4

Determination of cDNA and Amino Acid Sequence in Variable Region of Each Antibody To make clear what kind of amino acid sequence in the variable region has excellent properties as described in the above examples of AKL3H6 and AKL5C1 antibodies, the DNA in variable region of the L and H chains of each antibody using hybridoma was cloned and then the sequence thereof was determined. The cloning was performed by isolating RNA from the hybridoma using RNeasy Mini Kit available from QIAGEN Co., Ltd., performing a reverse transcription reaction using the TrueScript II RT available from Sawady Technology using random-9mer as a template, and amplifying the variable-region cDNA by the PCR method, using SuperTaq 2× kit available from Sawady Technology Co., Ltd., using the mix primer available from Novagen Co., Ltd. as 5'-primer and 5'-ACTGTTCAG-GACGCCATTTTGTCGTTCACT-3' (SEQ ID NO: 41) for the light chain and 5'-GGATCCAGAGTTCCAGGT-CACTGT-3' (SEQ ID NO: 42) for the heavy chain, as 3'-primers. The resulting DNA fragment was ligated using the DNA Ligation kit ver. 2 available from TaKaRa with pT7 Blue T-Vector available from Novagen Co., Ltd, and then it was used for transforming JM 109 competent cells available from TaKaRa Co., Ltd and seeded in X-gal-, ampicillin-, and IPTG-containing plates, followed by picking up white colonies. Plasmids were prepared from each of five species of clones that contains normal-sized inserts, respectively. After that, the DNA sequences were determined using an ABI PRISM 310-type automatic sequencer. The determined sequences showed the same sequences as those of five clones, except that a variation which may be caused by a PCR error was found in a part of them, so that these sequences were regarded as the objective DNA sequences. The results are shown in SEQ ID NO.: 11 to SEQ ID NO.: 18.

Furthermore, on the basis of the DNA sequences determined as described above, the results of the estimations of the amino acid sequences of the L and H chains are shown in SEQ ID NO.: 19 to SEQ ID NO.: 26, respectively.

Figure 4:
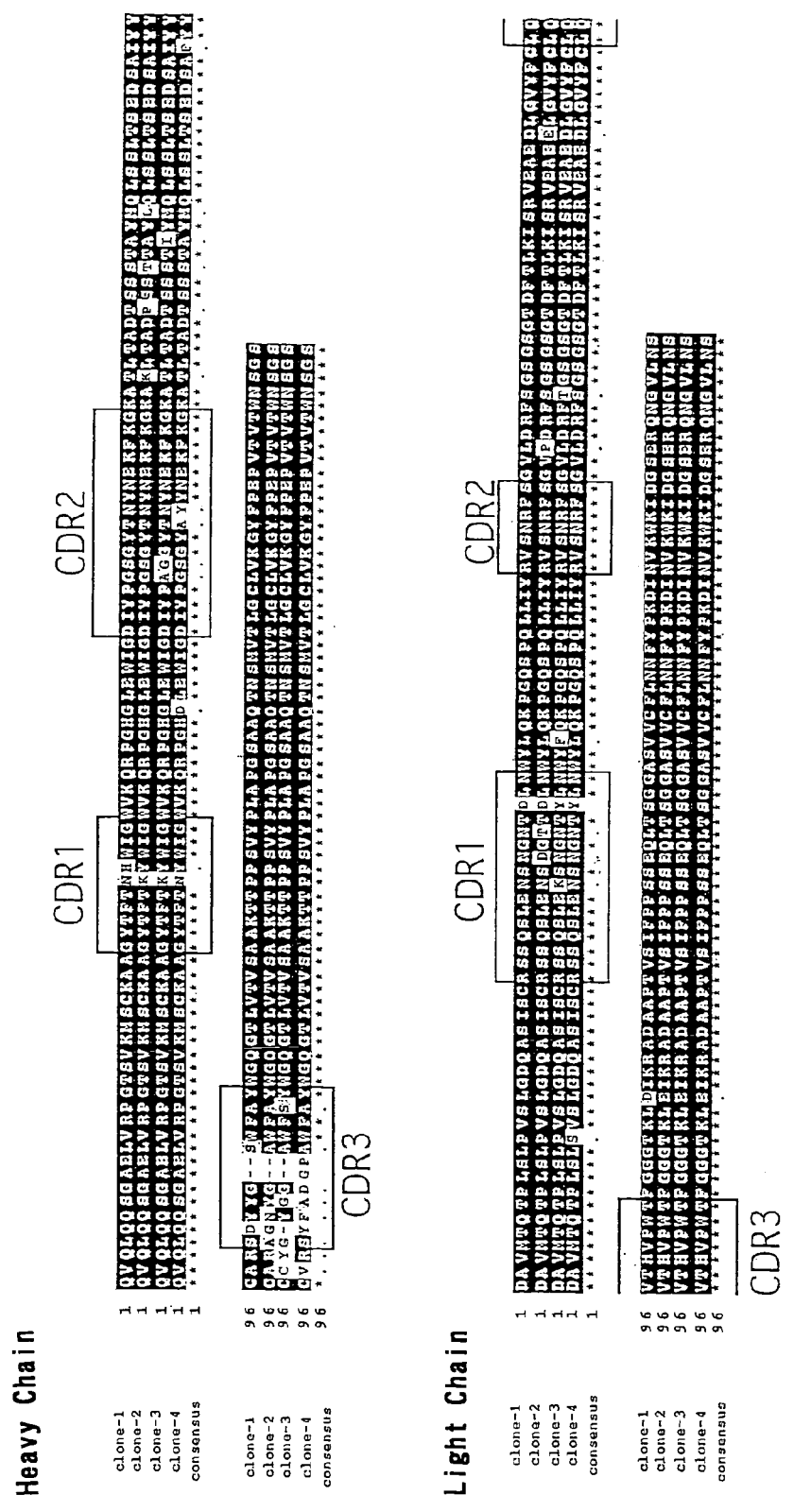

Furthermore, FIG. 4 shows the results of comparing amino acid sequences in the variable regions of the light and heavy chains in the respective antibodies by aligning the amino acid sequences. The amino acids were represented by means of a one-character notation. In addition, the complementarity determining regions in the variable region were surrounded by squares and represented by CDR 1 to 3, respectively.

As is obvious from this figure, each of four kinds of antibodies obtained by three independent immunologic operations has the common framework structure. Such a commonality seems to have something important with the acetyllysine recognition itself. On the other hand, the difference in the properties among the antibodies shown in Examples 1 and 2 seems to be attributed to a slight difference in their sequences described herein; however, since there is no three-dimensional information at present, it is not obvious which portion is responsible for the difference in the properties of the antibodies.

INDUSTRIAL APPLICABILITY

As the antibody of the present invention can detect acetyllysine without depending on the types of adjacent amino acids of acetyllysine so much, it is useful for detecting the state of acetylation of well-known various acetylated protein. For instance, it can be easily detected the change of acetylating level of histone under the influences of various stimulants by the method such as Western blotting. Furthermore, from the same reason, the antibody of the invention is very useful for detecting an unknown novel acetyllysine-containing protein. Concretely, by using an immunoprecipitation method using the antibody of the invention; or an affinity column, an antibody chip, or the like, on which the antibody of the invention is immobilized, it is expected that an unknown novel acetyllysine-containing protein would be found. Furthermore, as the antibody of the present invention is a monoclonal antibody, it can be altered to a single-chain antibody by an already-established method. Alternatively, as its epitope is acetyllysine and is small, there is a possibility that either a light chain or a heavy chain may have its activity, in this case, by means of a two-hybrid method using DNA encoding this, it can be used for detecting an acetyllysine-containing protein having a weak-affinity to the antibody. Furthermore, it may be used in a functional analysis on an acetyllysine-containing protein by expressing in various kinds of cells. Furthermore, if the presence of an acetylated protein having any connection with a pathologic condition is revealed in future, it will play an important role in establishment of a diagnosis method.

What is claimed is:

1. A monoclonal antibody recognizing an $N^{\epsilon}$-acetyllysine, comprising:

(1) a light chain comprising a constant region having an amino acid sequence represented by SEQ ID NO. 1 and a variable region having an amino acid sequence selected from the group consisting of SEQ ID NO. 2, SEQ ID NO. 5, SEQ ID NO. 6 and SEQ ID NO. 7; and (2) a heavy chain comprising a constant region having an amino acid sequence represented by SEQ ID NO. 3 and a variable region having an amino acid sequence selected from the group consisting of SEQ ID NO. 4, SEQ ID NO. 8, SEQ ID NO. 9 and SEQ ID NO. 10.

2. The monoclonal antibody according to claim 1, wherein the monoclonal antibody is a mouse monoclonal antibody.

3. A monoclonal antibody recognizing an $N^{\epsilon}$-acetyllysine, comprising:

(1) a light chain comprising a constant region having an amino acid sequence represented by SEQ ID NO. 1 and a variable region having an amino acid sequence represented SEQ ID NO. 7; and (2) a heavy chain comprising a constant region having an amino acid sequence represented by SEQ ID NO. 3 and a variable region having an amino acid sequence represented by SEQ ID NO. 10.

* * * * *